(12) United States Patent
Taniguchi et al.

(10) Patent No.: US 6,855,927 B2
(45) Date of Patent: Feb. 15, 2005

(54) METHOD AND APPARATUS FOR OBSERVING ELEMENT DISTRIBUTION

(75) Inventors: Yoshifumi Taniguchi, Hitachinaka (JP); Kazutoshi Kaji, Hitachi (JP); Yasumitsu Ueki, Hitachinaka (JP); Shigeto Isakozawa, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1 day.

(21) Appl. No.: 10/435,050

(22) Filed: May 12, 2003

(65) Prior Publication Data

US 2004/0000641 A1 Jan. 1, 2004

(30) Foreign Application Priority Data

May 13, 2002 (JP) .......................... 2002-136433

(51) Int. Cl.[7] .......................... H01J 37/28; G01N 23/04
(52) U.S. Cl. .......................... 250/305; 250/310; 250/311
(58) Field of Search .......................... 250/305, 310, 250/311

(56) References Cited

U.S. PATENT DOCUMENTS

| | | | |
|---|---|---|---|
| 4,740,704 A | | 4/1988 | Rose et al. |
| 4,743,756 A | | 5/1988 | Krivanek |
| 4,760,261 A | | 7/1988 | Rose et al. |
| 4,812,652 A | * | 3/1989 | Egle et al. .................. 250/311 |
| 5,449,914 A | | 9/1995 | Rose et al. |
| 5,981,948 A | * | 11/1999 | Taniguchi et al. .......... 250/311 |
| 6,066,852 A | | 5/2000 | Taya et al. |
| 6,150,657 A | | 11/2000 | Kimoto et al. |
| 2002/0033455 A1 | | 3/2002 | Rose |
| 2003/0085356 A1 | * | 5/2003 | Kaji et al. .................. 250/311 |

FOREIGN PATENT DOCUMENTS

| | | |
|---|---|---|
| JP | 62-66553 | 3/1987 |
| JP | 62-69456 | 3/1987 |
| JP | 07-021966 | 1/1995 |
| JP | 07-37536 | 2/1995 |
| JP | 11-73899 | 3/1999 |
| JP | 2001-148231 | 5/2001 |
| JP | 2001-243910 | 9/2001 |
| WO | WO 96/02935 | 1/1996 |

OTHER PUBLICATIONS

Krivanek, et al: "Developments in EELS instrumentation for spectroscopy and imaging", Microscopy, Microanalysis, Microstructures, Apr./Jun. 1991, vol. 2, pp. 315–332.

R. F. Egerton, "Electron Energy Loss Spectroscopy in the Electron Microscopy," pp. 27–45 (1986).

Ludwig Reimer (Ed.), "Energy–Filtering Transmission Electron Microscopy", *Springer Series in Optical Sciences*, vol. 71, pp. 47–55 (1995).

* cited by examiner

*Primary Examiner*—John R. Lee
*Assistant Examiner*—James J. Leybourne
(74) *Attorney, Agent, or Firm*—Dickstein Shapiro Morin & Oshinsky LLP

(57) ABSTRACT

There are provided an element distribution observing method and an element distribution observing apparatus under utilization of core-loss electrons capable of restricting artifact caused by either a thickness or density of a specimen, or an occurrence of the artifact caused by a diffraction contrast. Electron beam intensities in a total three different energy-loss areas of two energy-loss areas not containing any core-loss electrons and one energy-loss area are calculated to attain an element distribution on the basis of the corresponding three energy-loss areas and an electron beam intensity.

6 Claims, 4 Drawing Sheets

METHOD AND APPARATUS FOR OBSERVING ELEMENT DISTRIBUTION

BACKGROUND OF THE INVENTION

1. Field of the Invention

This invention relates to a method and apparatus for observing an element distribution and more particularly to a method and apparatus for observing an element distribution through computation under utilization of some core loss electrons.

2. Description of the Related Art

An incident electron beam sometimes loses energy under an interaction between the electron beam and a specimen. As this phenomenon, there are various kinds of methods such as a plasmon loss, a core loss and braking radiation, and their lost energy is different in reference to a structure of the specimen or the type of composing element and the like. In these methods, the core loss electron in particular showed a predetermined energy loss value in response to the type of element or their connected state and thus this core loss electron has been applied for observation of the element distribution or analysis of the connected state.

As an apparatus for analyzing an element under utilization of its energy loss, there have been provided an electron energy-loss spectroscopy (EELS) device (R. F. Egerton: Electron Energy-loss Spectroscopy in the Electron Microscope, Plenum Press (1986)) or an energy-filtering transmission electron microscopy (L. Reimer ed.: Energy-Filtering Transmission Electron Microscopy, Springer (1995)).

EELS device has a spectrometer for dividing energy of element in a spectroscopic manner mounted at a rear part of an observing apparatus utilizing some transmission electrons, such as a transmission electron microscope (TEM) or a scanning transmission electron microscope (STEM). As a well-known structure of the spectrometer, it has been disclosed in U.S. Pat. No. 4,743,756 and of Japanese Patent Laid-Open No. Hei 7-21,966.

As the energy-filtering transmission electron microscope, there have been provided an in-column type in which a focusing-type energy filter is inserted at the midway part of a focusing system of TEM, and a post-column type in which a focusing energy filter device is arranged at a rear part of the focusing system in TEM. As the in-column type, there have been provided Ω-type (Japanese Patent Laid-Open No. Sho 62-66,553), kα-type (Japanese Patent Laid-Open No. Sho 62-69,456), kγ-type (Laid-Open Patent Application WO 96/02935) and a mandolin-type (Japanese Patent Laid-Open No. Hei 7-37,536) or the like. Although as the post-column type, an apparatus called an imaging filter manufactured by GATAN Co., Ltd. (Gatan Imaging Filter: GIF (O. L. Krivanek. A. J. Gubbens and N. Dellby: Microsc. Microanal. Micostruct. vol. 2(1991)315.)) is the most famous device, there is also provided a system for drawing Ω-type orbit (Japanese Patent Laid-Open No. Hei 11-073899 and Japanese Patent Laid-Open No. 2001-243910).

A principle will be described at first in which an element distribution of specimen is attained under application of energy-loss electrons. At first, in FIG. 4 is indicated a typical energy-loss spectrum near the core loss energy. In the case that energy is lost during a method not related to an element such as a braking radiation or the like, a background having no specific energy loss value, but having a continuous spectrum is formed. This intensity J is approximately defined by the equation (1).

$$J = A \cdot \exp(-rE) \quad (1)$$

where, E is an energy loss value, and A and r are constants defined by a thickness of the specimen and its composition. Although an intensity of core-loss electrons is overlapped on this background, energy lost while exciting inner core electrons of the specimen is more than a minimum requisite energy for excitation, so that a shoulder called a core loss edge is normally formed in the energy loss spectrum. An image attained by an electron beam ranging from an energy loss area $E_1$ to $E_1 + \Delta E$ is defined as a pre-pre-edge image, an image attained by an electron beam ranging from an energy loss area $E_2$ to $E_2 + \Delta E$ is defined as a pre-edge image and an image attained by an electron beam ranging from an energy loss area $E_3$ to $E_3 + \Delta E$ is defined as a post-edge image. Since the pre-pre-edge image does not contain any core loss electrons, it is composed of only the background. When an intensity of the pre-pre-edge image is defined as $I_1$, a following equation of $$I_1 = \int_{E_1}^{E_1 + \Delta E} J dE = \int_{E_1}^{E_1 + \Delta E} A \cdot \exp(-r \cdot E) dE \quad (2)$$

$$= \frac{A}{r} \exp(-rE_1)\{1 - \exp(-r\Delta E)\}$$

Similarly, intensity $I_2$ of the pre-pre image becomes $$I_2 = \frac{A}{r} \exp(-rE_1)\exp(-r\delta E_1)\{1 - \exp(-r\Delta E)\} \quad (3)$$

$$= \exp(-r\delta E_1) I_1$$

When a core loss electron intensity contained in the post-edge image is defined as $I_e$ and a background intensity is defined as $I_{bk}$, an intensity $I_3$ of the post-edge image is obtained by the following equation:

$$I_3 = I_e + I_{bk} \quad (4)$$

$$= I_e + \exp(-r\delta E_2) I_2$$

When a contrast dependent on $I_e$ of the equation (4) can be calculated, an element distribution image can be attained.

(a) 3-Window Method:

At first, a ratio between the equation (3) and the equation (2), i.e. $R_1$ is defined as $R_1 = I_2/I_1 = \exp(-r\delta E_1)$, r becomes $$r = \frac{\ln R_1}{\delta E_1} \quad (5)$$

so that $I_e$ can be defined as $$I_e = I_3 - R_1^{\frac{\delta E_2}{\delta E_1}} I_2 \quad (6)$$

In particular, when an equation of $\delta E_1 = \delta E_2$ is defined, the equation (6) can be simplified as follows.

$$I_e = I_3 - \frac{I_2^2}{I_1} \quad (7)$$

This is a method called 3-window method and this is most widely used.

(b) Ratio Map Method

A ratio $R_2$ between the equation (4) and the equation (3), i.e. $R_2=I_3/I_2$ $$R_2 = \frac{I_e}{I_2} + \exp(-r\delta E_2) \qquad (8)$$

may also provide a measure in regard to an element. Because $I_e=0$ can be attained in an area having no element, so that only $\exp(-r\delta E_2)$ is attained and in turn, information on $I_e$ is overlaid in an area having an element. When r is constant in an observation area, only information $I_e$ becomes a contrast and is observed. This method is called either a Ration map or 2-window method.

(c) Spectrum Map Method

Although the aforesaid two types have been indicated on the basis of a total number of electrons in a certain energy area, if, the spectrum itself could be recorded, the background area is fitted by the equation (1) and a value $I_{bk}$ can be calculated more precisely. A method for recording all the spectra for every one point on the specimen under application of a scanning function of STEM and calculating $I_e$ for each of the points is called a spectrum mapping method.

(d) Imaging EELS Method

In the energy filter TEM, an energy loss area is determined under application of the energy selection slit. It is satisfactory to take a photograph of two images for the ratio mapping method and to take a photograph of three images for the 3-window method. However, it is also possible to take many photographs with a narrower slit and to attain an element distribution image under a procedure of the spectrum mapping method. This method is called an imaging ELS method.

In the gazette of Japanese Patent Laid-Open No. 2001-148231 is disclosed a structure for use in simultaneously detecting electron intensities in a plurality of energy loss areas. Upon detection of the electron intensities, it is possible to attain an element distribution image in concurrent with the STEM by calculating it not through software, but by an electric circuit.

Some features in the four types of element distribution image calculating methods described in the aforesaid prior art are indicated in Table 1. An independent detection in the Table is meant by a system for separately detecting an intensity of electron beam in a different energy loss area, and a simultaneous detection is meant by a system for detecting it under an application of a plurality of detection elements as described in the gazette of Japanese Patent Laid-Open No. 2001-148231. QE is meant by "quite excellent"; E is meant by "excellent"; and I is meant by "inferior", respectively. Artifact is meant by a false contrast generated in the case that r in the equation (8) is not kept constant, this artifact appears due to a mere difference in density even if the specimens have the same thickness to each other and this artifact applies a substantial influence against a quantitative characteristic. A diffraction contrast is meant by a phenomenon in which the number of electrons varies because the electron beams diffracted by the specimen are removed by an object iris diaphragm to influence against its quantitative characteristic. In the case of ratio map method, no influence is applied to a result even if an absolute amount changes because a ratio of the number of electrons is computed. However, in the case of other methods, it is necessary to pay an attention so as not to have any diffraction contrast at a stage of attaining an image before calculation because a subtraction method is to be carried out.

TABLE 1

Features of Method for Calculating Various Types of Element Distributions

| | Method | | | | | |
|---|---|---|---|---|---|---|
| | 3-window method | | Ratio map method | | Spectrum | |
| Item | Independent detection | Simultaneous detection | Independent detection | Simultaneous detection | map method | Imaging EELS |
| Quantitative characteristic | E | E | I | I | QE | E |
| Artifact | E | E | I | I | QE | E |
| Diffraction contrast | I | I | E | E | I | I |
| Preciseness | E | E | E | E | I | E |
| Sensitivity | E | E | E | B | QE | E |
| S/N | I | I | QE | QE | E | E |
| Speed | E | QE | E | QE | I | I |
| Positional alignment | E | QE | E | QE | I | I |
| Apparatus stability | E | QE | E | QE | I | I |

QE: Quite excellent,
E: Excellent,
I: Inferior

As apparent from this table, the method of the present invention has no superior characteristic in all items. The present invention becomes a powerful tool only through a simultaneous accomplishment of at least one merit in which the ratio map method is not influenced by a diffraction contrast and the other merit in which no artifact is present in other systems.

SUMMARY OF THE INVENTION

It is an object of the present invention to provide an element distribution observing method and an element distribution observing apparatus based on this method in which the aforesaid problems of the prior art are overcome, no artifact is present and it is not influenced by diffraction contrast.

In order to accomplish the aforesaid object, a feature of the present invention consists in providing means described below.

(1) Both items of the equation (6) are divided by $I_3$ to modify it to read $$\frac{R_2}{R_1^{\delta E_1}} = 1 + \frac{I_e}{I_{bk}} \quad (9)$$

where, $R_2=I_3/I_2$. That is r becoming a problem in the equation (8) is eliminated and no artifact is produced. In addition, even in the case that intensity is changed by the diffraction contrast, $I_e$ and $I_{bk}$ are changed in a proportional manner, so that influence of the diffraction contrast is cancelled and it does not appear in the image. Additionally, in the case of an equation of $\delta E_1=\delta E_2$, it becomes a more simple equation of $$\frac{R_2}{R_1} = 1 + \frac{I_e}{I_{bk}} \quad (10)$$

Such a configuration as above does not produce any artifact and enables an element distribution image not producing any influence in diffraction contrast to be calculated.

(2) In either TEM or STEM having an EELS device capable of detecting simultaneously electron intensities of three different energy loss areas under application of a plurality of detector elements described in Japanese Patent Laid-Open No. 2001-148231, some energy loss spectra on a plane of the specimen are collected while scanning the incident electron beams and then an element distribution image is calculated under application of either the equation (9) or the equation (10) using the intensity signals from these detectors.

Such a configuration as above does not produce any artifact and further enables an element distribution image having no diffraction contrast to be observed.

3) In either TEM or STEM having the EELS device mounted, the energy loss spectra are collected while scanning incident electron beams on the specimen plane so as to calculate electron beam intensities of areas corresponding to the post-edge image, pre-edge image and pre-pre-edge image and calculate an element distribution image under application of either the equation (9) or the equation (10).

Such a configuration as above does not produce any artifact and further enables an element distribution image having no diffraction contrast to be observed.

(4) In the energy filter TEM, the post-edge image, pre-edge image and pre-pre-edge image are photographed in the same manner as that of 3-Window method, and an element distribution image is calculated under application of either the equation (9) or the equation (10).

Such a configuration as above does not produce any artifact and further enables an element distribution image having no diffraction contrast to be observed.

DESCRIPTION OF THE PREFERRED EMBODIMENTS

Figure 1:
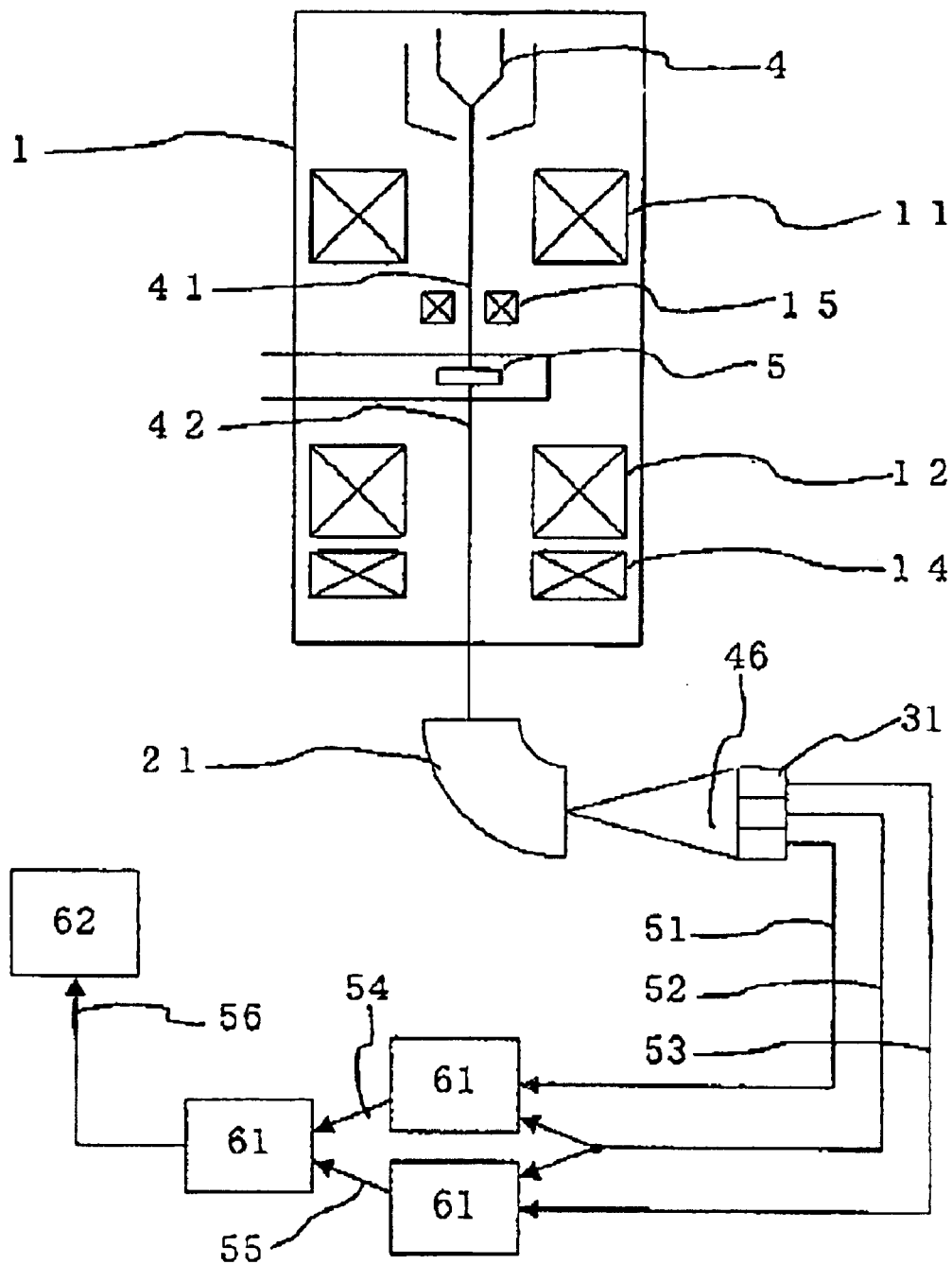
FIG. 1 is an illustrative view for showing a first embodiment of the present invention.

Referring now to the drawings, some embodiments of the present invention will be described in detail as follows.

Figure 4:
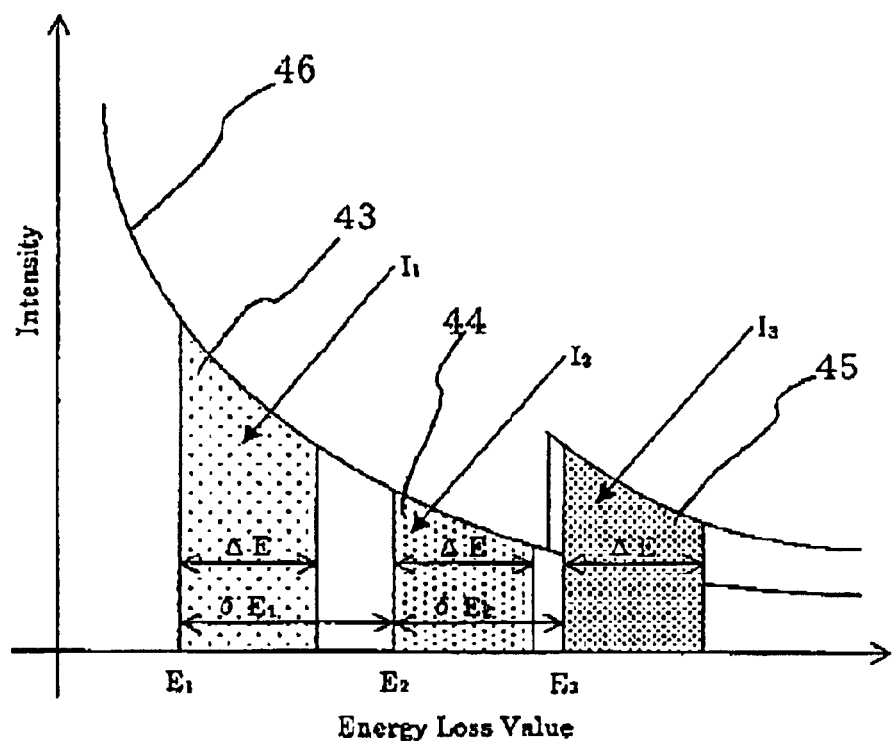
FIG. 4 is an illustrative diagram for showing a typical energy loss spectrum.

FIG. 1 is an illustrative view for showing a first embodiment of the present invention. This embodiment is made such that the present invention is applied to an STEM device 1. Radiation electron beam 41 radiated from an electron gun 4 is radiated onto a specimen 5 through a radiation lens system 11. A deflector coil 15 scans a radiating position on the specimen 5. Only a requisite dispersion angle of a transmission electron beam 42 transmitted through the specimen 5 is incident to a spectrometer 21 through an objective lens 12 and a projecting lens system 14. The spectrometer 21 forms an energy loss spectrum 46 (FIG. 4) in response to energy lost at the specimen 5. An electron beam simultaneous sensor 31 converts an intensity of electron beam contained in a first energy loss area 43 (FIG. 4), a second energy loss area 44 and a third energy loss area 45 (FIG. 4) of the energy loss spectrum 46 into light to generate an electron intensity signal ($I_1$) 51 in the first energy loss area, an electron intensity signal ($I_2$) 52 in the second energy loss area and an electron intensity signal ($I_3$) 53 in the third energy loss, respectively. An electric circuit for inputting one electron intensity signal and outputting its ratio constitutes a signal intensity divider 61. Intensity signals 51, 52 are inputted to one signal intensity divider 61. Intensity signals 52, 53 are inputted to the other signal intensity divider 61 so as to generate a signal intensity ratio $R_1=I_2/I_1$ 54 of the second and first signals and a signal intensity ratio $R_2=I_3/I_2$ 55 of the third and second signals. Signals 54 and 55 are inputted to the other signal intensity divider 61 to generate a ratio of $R_2/R_1$. This is an element distribution signal 56 defined by the equation (10). It becomes possible to display an element distribution image at an element distribution display device 62 by synchronizing with a scanning performed by the deflector coil 15. Calculation can be carried out in a quite high speed because an electric circuit constitutes the element distribution. When the deflector coil 15 scans it in a high precision manner, a high precision element distribution image can be rapidly attained.

Figure 2:
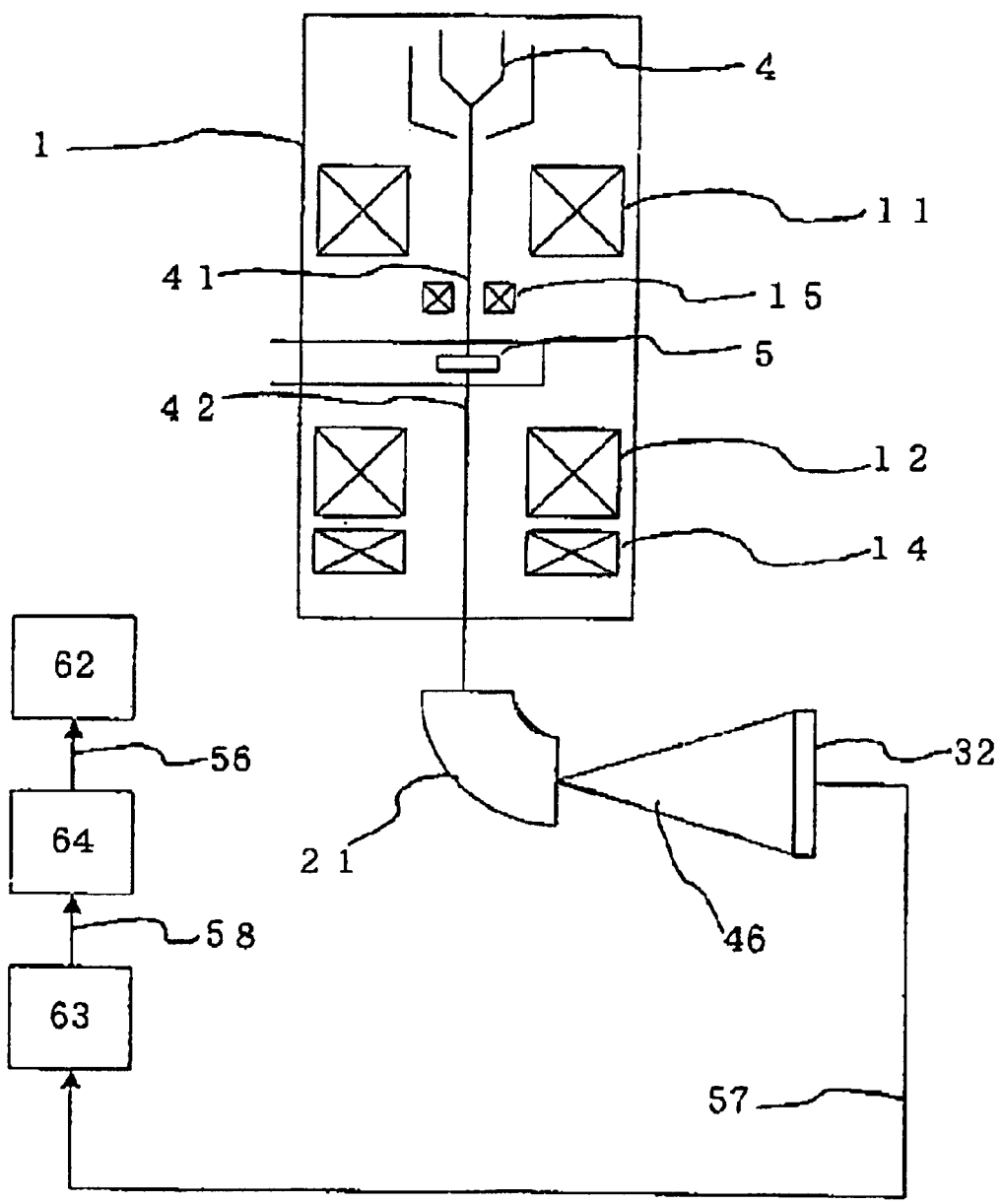
FIG. 2 is an illustrative view for showing a second embodiment of the present invention.

FIG. 2 is an illustrative view for showing a second embodiment of the present invention. This second embodiment is the same as that of the first embodiment in view of its circumstance ranging from a spectroscopic operation of the transmission electron beam 42 with the spectrometer 21 to a formation of the energy loss spectrum 46. A spectrum detector 32 converts the spectrum 46 into an energy loss spectrum signal 57 and outputs it. A spectrum-recording device 63 records an energy loss spectrum signal 57, calculates electron beam intensities 58 in different three energy areas from it and delivers them to a calculating device 64. The calculating device 64 calculates an element analysis in response to definitions in the equations (9) and (10) and outputs an element distribution signal 56. An element distribution display device 62 displays the element distribution signal 56. Displaying of image in correspondence with information on position of the specimen 5 through the deflection coil 15 also enables the element distribution image to be displayed at the element distribution display device 62.

Figure 3:
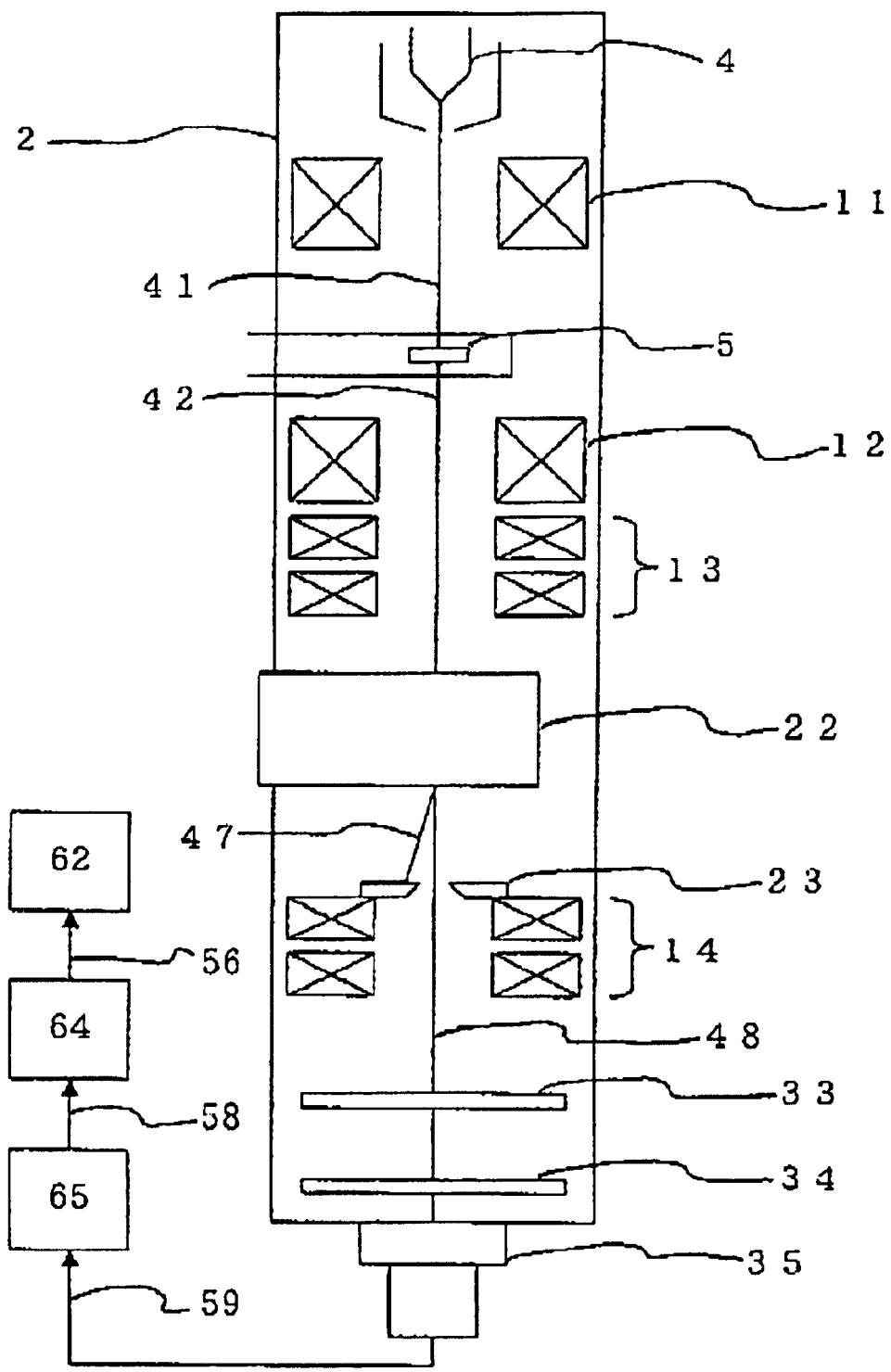
FIG. 3 is an illustrative view for showing a third embodiment of the present invention.

FIG. 3 is an illustrative view for showing a third embodiment of the present invention. This is an embodiment in which the present invention is applied to an in-column type energy filter TEM device 2. After passing through the specimen 5, the transmission electron beam 42 is focused by an object lens 12 and intermediate lens systems 13 and then its energy is divided in a spectroscopic manner by an energy filter 22. An energy selection slit 23 passes only an electron beam 48 in a requisite energy area and eliminates an electron beam 47 other than the former. A projection lens system 14 focuses electrons 48 selected by the energy selection slit as an energy filter image. The energy filter image can also be observed on a fluorescent plate 33 and further photographed by a photograph film 34 or an SSCCD 35. The SSCCD 35 photographed energy filter images in different three energy loss areas outputs an energy filter image signal 59, and an energy filter image recorder device 65 records three energy filter images. The energy filter image recorder device 65 delivers a recorded electron beam intensity signal 58 of each of the recorded energy loss areas and the calculator device 64 calculates an element distribution in response to a definition defined by either the equation (9) or the equation (10) and outputs an element distribution signal 56. The element distribution display device 62 displays the element distribution signal 56. In this embodiment, the in-column type energy filter TEM has been described. However, it is also possible to apply it to a post-column type energy filter TEM.

As described above, the present invention can provide some following effects.

(1) The element distribution is calculated by a computation defined by either the equation (9) or the equation (10). Such a configuration as above does not produce any artifact and enables an element distribution image not producing any influence in diffraction contrast to be computed.

(2) In either TEM or STEM having an EELS device capable of detecting simultaneously electron intensities of three different energy loss areas under application of a plurality of detector elements described in Japanese Patent Laid-Open No. 2001-148231, some energy loss spectra are collected while scanning the incident electron beams on a plane of the specimen and then an element distribution image is calculated under application of either the equation (9) or the equation (10) using the intensity signals from these detectors.

Such a configuration as above does not produce any artifact and further enables an element distribution image having no diffraction contrast to be observed.

(3) In either TEM or STEM having the EELS device mounted, the energy loss spectra are collected while scanning incident electron beams on the specimen plane so as to calculate electron beam intensities of areas corresponding to the post-edge image, pre-edge image and pre-pre-edge image and calculate an element distribution image under application of either the equation (9) or the equation (10).

Such a configuration as above does not produce any artifact and further enables an element distribution image having no diffraction contrast to be observed.

(4) In the energy filter TEM, the post-edge image, pre-edge image and pre-pre-edge image are photographed in the same manner as that of 3-Window method, and an element distribution image is calculated under application of either the equation (9) or the equation (10).

Such a configuration as above does not produce any artifact and further enables an element distribution image having no diffraction contrast to be observed.

What is claimed is:

1. A method for observing an element distribution in which an electron beam passed through a specimen is divided in its energy in a spectroscopic manner and the element distribution is attained in reference to intensities of electron beams contained in different three energy areas, wherein the element distribution is attained by calculating $R_2 \div R_1$ $(\delta E_2 \div \delta E_1)$ where a first energy area ranges from $E_1$ to $E_1 + \Delta E$, a second energy area ranges from $E_2$ to $E_2 + \Delta E$ and a third energy area ranges from $E_3$ to $E_3 + \Delta E$;

a core loss electron of a target element is contained in the third energy area;

equations of $E_2 - E_1 = \delta E_1$ and $E_3 - E_2 = \delta E_2$ are established;

an intensity of electron beam contained in the first energy area is $I_1$, an intensity of electron beam contained in the second energy area is $I_2$ and an intensity of electron beam contained in the third energy area is $I_3$; and equations of $R_1 = I_2 \div I_1$ and $R_2 = I_3 \div I_2$ are established.

2. A method for observing an element distribution in which an electron beam passed through a specimen is divided in its energy in a spectroscopic manner and the element distribution is attained in reference to intensities of electron beams contained in different three energy areas, wherein the element distribution is attained by calculating $R_2 \div R_1$ where a first energy area ranges from $E_1$ to $E_1 + \Delta E$, a second energy area ranges from $E_2$ to $E_2 + \Delta E$ and a third energy area ranges from $E_3$ to $E_3 + \Delta E$;

a core loss electron of a target element is contained in the third energy area;

equations of $E_2 - E_1 = E_3 - E_2 = \Delta E$ are established;

an intensity of electron beam contained in the first energy area is $I_1$, an intensity of electron beam contained in the second energy area is $I_2$ and an intensity of electron beam contained in the third energy area is $I_3$; and equations of $R_1 = I_2 \div I_1$ and $R_2 = I_3 \div I_2$ are established.

3. An apparatus for observing an element distribution comprised of an electron gun; a radiation electron optical system for radiating an incident electron beam radiated from said electron gun against a specimen; a first focusing electron optical system for focusing a transmission electron beam passed through said specimen; an energy filter for dividing energy of said transmission electron beam in a spectroscopic manner; a mechanism for selecting only an electron beam having a specified energy in the electron beams divided in its energy in a spectroscopic manner; a second focusing electron optical system for focusing said energy selected electron beam to form an energy filter image; an image observing and recording means for observing and recording said energy filter image; and a calculating means for calculating said energy filter image recorded by said image observing and recording means to attain an element distribution, wherein said calculating means attains an element distribution image using a method for observing an element distribution in which an electron beam passed through a specimen is divided in its energy in a spectroscopic manner and the element distribution is attained in reference to intensities of electron beams contained in different three energy area by calculating $R_2 \div R_1$ $(\delta E_2 \div \delta E_1)$ where a first energy area ranges from $E_1$ to $E_1 + \Delta E$, a second energy area ranges from $E_2$ to $E_2 + \Delta E$ and a third energy area ranges from $E_3$ to $E_3 + \Delta E$;

a core loss electron of a target element is contained in the third energy area;

equations of $E_2-E_1=\delta E_1$ and $E_3-E_2=\delta E_2$ are established;

an intensity of electron beam contained in the first energy area is $I_1$, an intensity of electron beam contained in the second energy area is $I_2$ and an intensity of electron beam contained in the third energy area is $I_3$, and equations of $R_1=I_2 \div I_1$ and $R_2=I_3 \div I_2$ are established.

4. An apparatus for observing an element distribution comprised of an electron gun; a radiation electron optical system for radiating an incident electron beam radiated from said electron gun against a specimen; a first focusing electron optical system for focusing a transmission electron beam passed through said specimen; an energy filter for dividing energy of said transmission electron beam in a spectroscopic manner; a mechanism for selecting only an electron beam having a specified energy in the electron beams divided in its energy in a spectroscopic manner; a second focusing electron optical system for focusing said energy selected electron beam to form an energy filter image; an image observing and recording means for observing and recording said energy filter image; and a calculating means for calculating said energy filter image recorded by said image observing and recording means to attain an element distribution, wherein said calculating means attains an element distribution image using a method for observing an element distribution in which an electron beam passed through a specimen is divided in its energy in a spectroscopic manner and the element distribution is attained in reference to intensities of electron beams contained in different three energy area by calculating $R_2 \div R_1$ where a first energy area ranges from $E_1$ to $E_1+\Delta E$, a second energy area ranges from $E_2$ to $E_2+\Delta E$ and a third energy area ranges from $E_3$ to $E_3+\Delta E$;

a core loss electron of a target element is contained in the third energy area;

equations of $E_2-E_1=E_3-E_2=\Delta E$ are established;

an intensity of electron beam contained in the first energy area is $I_1$, an intensity of electron beam contained in the second energy area is $I_2$ and an intensity of electron beam contained in the third energy area is $I_3$; and equations of $R_1=I_2 \div I_1$ and $R_2=I_3 \div I_2$ are established.

5. An apparatus for observing an element distribution comprised of an electron gun; a radiation electron optical system for radiating an incident electron beam radiated from said electron gun against a specimen; an electron beam scanning means for scanning said incident electron beam on a plane of said specimen plane; an energy spectrometer for dividing energy of a transmission electron beam passed through said specimen in a spectroscopic manner; a spectrum recording means for recording an energy loss spectrum formed by said energy spectrometer in synchronization with said electron beam scanning means; and a calculating means for calculating said energy loss spectrum recorded by said spectrum recording means to attain an element distribution, wherein said calculating means attains an element distribution image using a method for observing an element distribution in which an electron beam passed through a specimen is divided in its energy in a spectroscopic manner and the element distribution is attained in reference to intensities of electron beams contained in different three energy area by calculating $R_2 \div R_1(\delta E_2 \div \delta E_1)$ where a first energy area ranges from $E_1$ to $E_1+\Delta E$, a second energy area ranges from $E_2$ to $E_2+\Delta E$ and a third energy area ranges from $E_3$ to $E_3+\Delta E$;

a core loss electron of a target element is contained in the third energy area;

equations of $E_2-E_1=\delta E_1$ and $E_3-E_2=\delta E_2$ are established;

an intensity of electron beam contained in the first energy area is $I_1$, an intensity of electron beam contained in the second energy area is $I_2$ and an intensity of electron beam contained in the third energy area is $I_3$; and equations of $R_1=I_2 \div I_1$ and $R_2=I_3 \div I_2$ are established.

6. An apparatus for observing an element distribution comprised of an electron gun; a radiation electron optical system for radiating an incident electron beam radiated from said electron gun against a specimen; an electron beam scanning means for scanning said incident electron beam on a plane of said specimen plane; an energy spectrometer for dividing energy of a transmission electron beam passed through said specimen in a spectroscopic manner; a spectrum recording means for recording an energy loss spectrum formed by said energy spectrometer in synchronization with said electron beam scanning means; and a calculating means for calculating said energy loss spectrum recorded by said spectrum recording means to attain an element distribution, wherein said calculating means attains an element distribution image using a method for observing an element distribution in which an electron beam passed through a specimen is divided in its energy in a spectroscopic manner and the element distribution is attained in reference to intensities of electron beams contained in different three energy area by calculating $R_2 \div R_1$ where a first energy area ranges from $E_1$ to $E_1+\Delta E$, a second energy area ranges from $E_2$ to $E_2+\Delta E$ and a third energy area ranges from $E_3$ to $E_3+\Delta E$;

a core loss electron of a target element is contained in the third energy area;

equations of $E_2-E_1=E_3-E_2=\Delta E$ are established;

an intensity of electron beam contained in the first energy area is $I_1$, an intensity of electron beam contained in the second energy area is $I_2$ and an intensity of electron beam contained in the third energy area is $I_3$; and equations of $R_1=I_2 \div I_1$ and $R_2=I_3 \div I_2$ are established.

* * * * *

UNITED STATES PATENT AND TRADEMARK OFFICE
CERTIFICATE OF CORRECTION

PATENT NO.     : 6,855,927 B2
DATED          : February 15, 2005
INVENTOR(S)    : Yoshifumi Taniguchi et al.

It is certified that error appears in the above-identified patent and that said Letters Patent is hereby corrected as shown below:

Column 10,
Line 52, the following claims are added:

--7. An apparatus for observing an element distribution comprised of an electron gun; a radiation electron optical system for radiating an incident electron beam radiated from said electron gun against a specimen; an electron beam scanning means for scanning said incident electron beam on a plane of said specimen plane; an energy spectrometer for dividing energy of a transmission electron beam passed through said specimen in a spectroscopic manner; three electron beam intensity detector means for converting electron beam intensities of three different energy areas of the energy loss spectra formed by said energy spectrometer into the number of photons approximately proportional to them; and a calculating means for calculating electron beam intensities in said three different energy areas of said energy loss spectra detected by said electron beam intensity detector means, wherein said calculating means attains an element distribution image using a method for observing an element distribution in which an electron beam passed through a specimen is divided in its energy in a spectroscopic manner and the element distribution is attained in reference to intensities of electron beams contained in different three energy area by calculating $R_2 + R_1 (\delta E_2 + \delta E_1)$ where a first energy area ranges from $E_1$ to $E_1 + \Delta E$, a second energy area ranges from $E_2$ to $E_2 + \Delta E$ and a third energy area ranges from $E_3$ to $E_3 + \Delta E$;

a core loss electron of a target element is contained in the third energy area;

equations of $E_2 - E_1 = \delta E_1$ and $E_3 - E_2 = \delta E_2$ are established;

an intensity of electron beam contained in the first energy area is $I_1$, an intensity of electron beam contained in the second energy area is $I_2$ and an intensity of electron beam contained in the third energy area is $I_3$; and equations of $R_1 = I_2 + I_1$ and $R_2 = I_3 + I_2$ are established in synchronous with said electron beam scanning means.

UNITED STATES PATENT AND TRADEMARK OFFICE
CERTIFICATE OF CORRECTION

PATENT NO.    : 6,855,927 B2
DATED         : February 15, 2005
INVENTOR(S)   : Yoshifumi Taniguchi et al.

It is certified that error appears in the above-identified patent and that said Letters Patent is hereby corrected as shown below:

Column 10 (cont'd),

8. An apparatus for observing an element distribution comprised of an electron gun; a radiation electron optical system for radiating an incident electron beam radiated from said electron gun against a specimen; an electron beam scanning means for scanning said incident electron beam on a plane of said specimen plane; an energy spectrometer for dividing energy of a transmission electron beam passed through said specimen in a spectroscopic manner; three electron beam intensity detector means for converting electron beam intensities of three different energy areas of the energy loss spectra formed by said energy spectrometer into the number of photons approximately proportional to them; and a calculating means for calculating electron beam intensities in said three different energy areas of said energy loss spectra detected by said electron beam intensity detector means, wherein said calculating means attains an element distribution image using a method for observing an element distribution in which an electron beam passed through a specimen is divided in its energy in a spectroscopic manner and the element distribution is attained in reference to intensities of electron beams contained in different three energy area by calculating $R_2 + R_1$ where a first energy area ranges from $E_1$ to $E_1 + \Delta E$, a second energy area ranges from $E_2$ to $E_2 + \Delta E$ and a third energy area ranges from $E_3$ to $E_3 + \Delta E$;

a core loss electron of a target element is contained in the third energy area;

equations of $E_2 - E_1 = E_3 - E_2 = \Delta E$ are established;

UNITED STATES PATENT AND TRADEMARK OFFICE
CERTIFICATE OF CORRECTION

PATENT NO.    : 6,855,927 B2
DATED         : February 15, 2005
INVENTOR(S)   : Yoshifumi Taniguchi et al.

It is certified that error appears in the above-identified patent and that said Letters Patent is hereby corrected as shown below:

Column 10 (cont'd), an intensity of electron beam contained in the first energy area is $I_1$, an intensity of electron beam contained in the second energy area is $I_2$ and an intensity of electron beam contained in the third energy area is $I_3$; and equations of $R_1 = I_2 + I_1$ and $R_2 = I_3 + I_2$ are established in synchronous with said electron beam scanning means.--

Signed and Sealed this

Eighteenth Day of October, 2005

JON W. DUDAS
*Director of the United States Patent and Trademark Office*